United States Patent [19]

Pegg et al.

[11] Patent Number: 4,649,918
[45] Date of Patent: Mar. 17, 1987

[54] BONE CORE REMOVING TOOL

[75] Inventors: Robert J. Pegg; William L. Gaertner, Jr., both of Williamsburg, Va.

[73] Assignee: Custom Medical Devices, Inc., Newport News, Va.

[21] Appl. No.: 389,886

[22] Filed: Jun. 18, 1982

Related U.S. Application Data

[63] Continuation of Ser. No. 183,954, Sep. 3, 1980, abandoned.

[51] Int. Cl.[4] .............................................. A61B 17/32
[52] U.S. Cl. ...................................... 128/305; 128/754
[58] Field of Search ................ 128/92 EC, 92 E, 753, 128/754, 305, 310, 305.1; 30/113.1, 113.2, 316

[56] References Cited

U.S. PATENT DOCUMENTS

| | | | |
|---|---|---|---|
| 185,902 | 1/1877 | Fallows | 30/113.1 |
| 1,162,669 | 11/1915 | Vinnedge | 128/310 |
| 1,977,017 | 10/1934 | Schiller | 30/316 X |
| 3,577,979 | 5/1971 | van der Gaast | 128/754 |
| 3,628,524 | 12/1971 | Jamshidi | 128/754 |
| 3,850,158 | 11/1974 | Elias et al. | 128/310 X |
| 4,122,855 | 10/1978 | Tezel | 128/310 |
| 4,314,565 | 2/1982 | Lee | 128/753 |

Primary Examiner—Michael H. Thaler
Attorney, Agent, or Firm—Cushman, Darby & Cushman

[57] ABSTRACT

A bone core removing tool with a stainless steel cylinder having an internal bore extending along the cylindrical axis from an externally honed cutting edge for cutting a core of bone which is pushed into the bore as the tool is driven into a bone and a plurality of radially inwardly extending teeth within the bone adjacent the edge for preventing rotation of the core to permit removal of the core by rotating the tool to break the core at the cutting edge.

9 Claims, 3 Drawing Figures

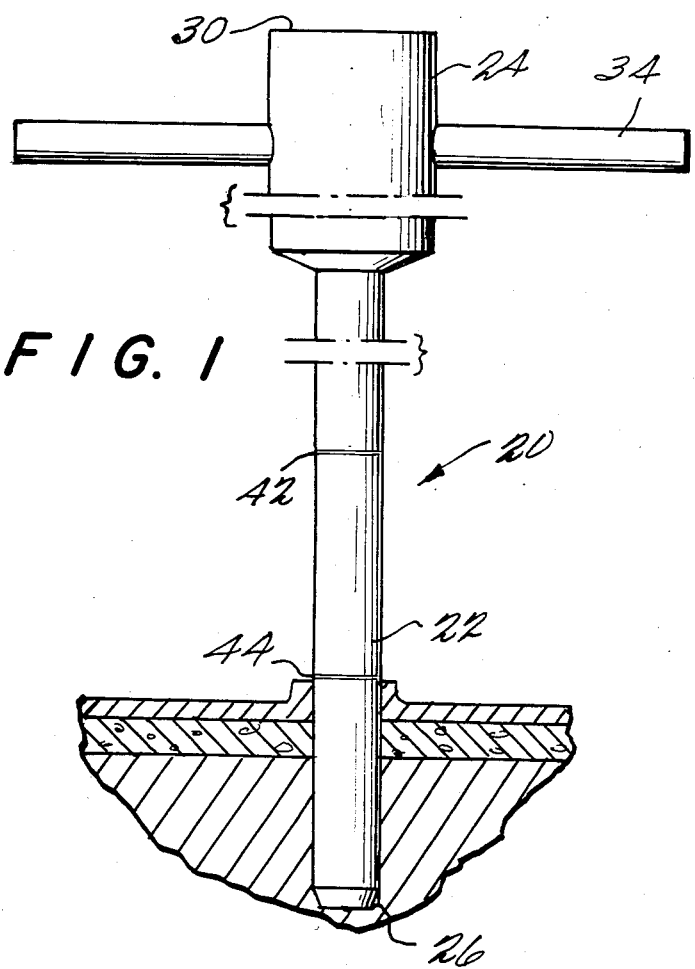
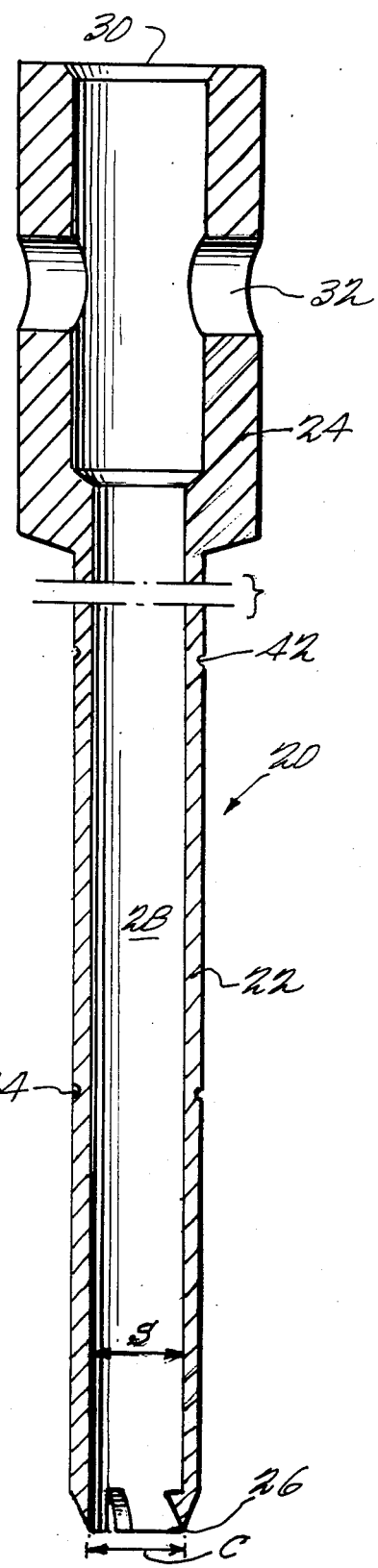
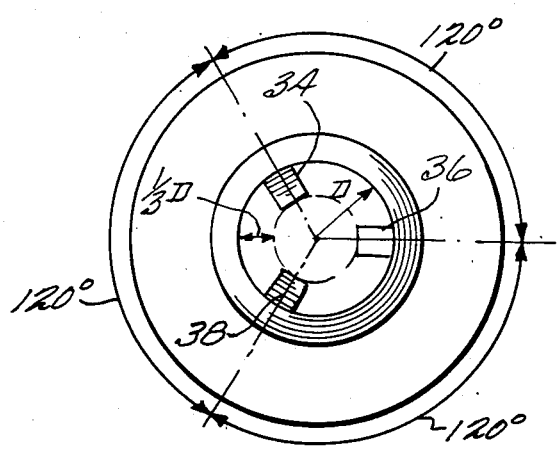

BONE CORE REMOVING TOOL

This is a continuation of application Ser. No. 183,954 filed Sept. 3, 1980, now abandoned.

BACKGROUND AND SUMMARY OF THE INVENTION

The invention relates to a tool for removing a core of bone and more particularly for enabling a surgeon to remove a cylindrical core of bone in vivo from a patient.

One relatively common surgical procedure calls for removal of a cylindrical core of medulla bone from a living patient and grafting elsewhere in the patient's or someone else's body. This is accomplished by making a minimal incision over the illiac crest and then driving a cutting tool into the bone to remove a core.

A variety of such instruments have been proposed in the past for removing bone segments and cores. For example, the patent to Velasco 847,133 describes an arrangement with a springloaded extractor for withdrawing a disc-shaped fragment of bone. The patents to Ackermann 2,919,692 and Elias et al 3,850,158 show other medical tools for extracting fragments of bone.

The present invention relates to a unique tool which has a number of substantial advantages in comparison with tools utilized in the past. According to the present invention, the tool is formed as a metal cylinder, preferably of stainless steel, having an internal bore extending along the cylindrical axis from an externally honed cutting edge. After insertion through a minimal incision, the tool is driven into the bone by the surgeon so that a core of bone is pushed into the bore. Utilizing an externally honed cutting edge insures that the bone is not compressed within the bore and may freely enter the same. A plurality of radially extending teeth, for example, three teeth separated by 120° are provided within the bore adjacent the edge for preventing rotation of the core.

A second bore extends laterally through the instrument for receiving an extraction handle. When the tool has been driven to the desired depth, the insertion handle is placed through this laterally extending bore and the tool rotated. The radially extending teeth prevent rotation of the core which, accordingly, breaks at the cutting edge. The teeth further engage the core as it attempts to rotate so that the core can now be easily removed intact with the tool. The teeth also form grooves along the length of the core bone which, after grafting is complete, provide additional bone strength as the three grooves are filled with corticle bone. In addition, these channels provide a means of equalizing the pressure within the bone so that the core can be more easily removed.

Other objects and purposes of the invention will become clear from the following detailed description of the drawings.

BRIEF DESCRIPTION OF THE DRAWINGS

FIG. 1 shows the unique tool of the present invention with an extracting handle therein, schematically being driven into a bone of a living patient during a surgical procedure;

FIG. 2 shows a sectional view of the tool of FIG. 1; and

FIG. 3 shows an end view of the tool of FIGS. 1 and 2.

DETAILED DESCRIPTION OF THE DRAWINGS

Reference is now made to FIGS. 1–3 which illustrate one embodiment of the present invention. The bone removing tool 20 is a cylindrical cutting tool made out of a single piece of surgical stainless steel and formed into a first cylindrical portion 22 and a second cylindrical portion 24 with the second portion being of greater external diameter than the first. For example, in a preferred embodiment, the tool measures five inches long and is heat treated to a Rockwell hardness of approximately 50. The external diameter of the portion 24 is three-quarters of an inch and portion 24 is one and one-half inches long. The external diameter of portion 22 varies according to the desired size of the tool. A set of two tools having internal diameters of one-fourth inch, and three-sixteenths inch have been found to be satisfactory for most surgeons. The portion 22 in the preferred embodiment measures three and one-half inches in length. The end of portion 22 is honed externally to a sharp cutting edge 26.

As shown in FIG. 2, an internal bore 28 extends from cutting edge 26 to an opposite end 30 from which bone can be removed by the surgeon after the extraction has been carried out. A second bore 32 extends through the portion 24 laterally to the axis of the cylinder for receiving the extraction handle 34 shown in FIG. 1. Handle 34 can be a one-fourth inch diameter handle which is inserted after the cutting tool has been driven to the desired depth and used for rotating the tool to cause the bone to break at the cutting edge 26. Bore 32 may, for example, by one-fourth inch in diameter, and the extraction handle 34, four inches long.

Cutting edge 26 of the tool of the present invention is externally honed so that the surrounding bone is forced to compress and the bone entering bore 28 is cut free from the surrounding bone and is not forced to compress. Thus, the bone core within bore 28 can pass freely into that diameter and out the opposite end after the procedure has been completed. A slight taper is machined into cylindrical portion 22 in the direction from cutting edge 26 to portion 24 so that there is a minimum trauma to the surrounding bone as the tool is forced into the bone.

Just inside cutting edge 26 are three teeth 34, 36 and 38 which extend inwardly and radially, preferably filling about 10% to 20% of the cross-sectional area of the bore 28. At least two such teeth are preferred, and more than three can be employed if desired. When the tool is rotated using handle 34, the core of the bone is forced to break loose from the surrounding bone at cutting edge 26. In addition, when the tool is rotated, teeth 34, 36 and 38 embed into the core bone so that when the tool is extracted, the bone core is extracted with it. An added function of the teeth is that they cut grooves along the length of the core bone as it passes through the center diameter of the tool. With time, after grafting is complete, the medulla core bone forms a hard surface of corticle bone. The three grooves filled with corticle bone provide additional bone strength.

A short distance from the cutting edge within the bore 28 the internal diameter is slightly enlarged, for example by approximately 0.01 inch. This enlarged diameter enables the surgeon to easily push the bone core through the internal diameter and out the end of the tool opposite that from which it entered. A oneeighth inch diameter ramrod (not shown) can be utilized to carry out this pushing.

Circumscribed around the tool shaft at one inch intervals are grooves in a plane transverse to the cylindrical axis, for example, grooves 42 and 44 for indicating to the surgeon the depth into the bone that the tool has been driven.

A surface cutter (not shown) is preferably included in the set so that the doctor has an instrument for cutting the corticle or bone surface. This tool has an internally honed cutting edge so that the surrounding bone is not expanded whtn the corticle cap is cut out.

Many changes and modifications in the above-described embodiment of the invention can, of course, be carried out without departing from the scope thereof. Accordingly, that scope is intended to be limited only by the scope of the appended claims.

What is claimed is:

1. A bone core removing tool comprising a metal cylindrical tool having an internal surface defining an internal bore extending along the cylindrical axis of said tool from an externally honed cutting edge for cutting a core of bone which is pushed into said bore as said tool is driven into a bone and having a plurality of longitudinally oriented teeth positioned about 120° apart and extending inwardly from said surface at the cutting edge into said bore filling between ten and twenty percent of the cross sectional area of said bore for preventing rotation of a core in said bore with respect to said bore to permit separation of said core from said bone by rotation of said tool, said teeth each being defined between longitudinally extending surfaces disposed in parallel planes so that each tooth is non-tapering in the radial direction.

2. A tool as in claim 1, wherein said tool has a hole extending therethrough transverse to said cylindrical axis for receiving an extraction handle for rotating said tool and cutting the core at the cutting edge.

3. A tool as in claim 2, further including said extraction handle.

4. A tool as in claim 1, wherein said tool is stainless steel.

5. A tool as in claim 1 wherein said tool includes a first cylindrical portion extending from said cutting edge and a second cylindrical portion extending from said first portion, said second portion having a diameter greater than said first portion and being coaxial with said first portion.

6. A tool as in claim 1, wherein the internal diameter of said bore increases from said cutting edge so that said core may be easily removed from the end opposite from that which it entered.

7. A tool as in claim 1 including a plurality of grooves around the outside periphery of said tool in a plane transverse to said axis to indicate the depth of penetration into a bone.

8. A tool as in claim 1, wherein said bore extends through said tool from said cutting edge to an opposite end.

9. A tool as in claim 1, wherein the external surface of said tool is slightly tapered in the direction from said cutting edge.

* * * * *